(12) United States Patent
Hayes

(10) Patent No.: US 10,405,974 B2
(45) Date of Patent: Sep. 10, 2019

(54) REPLACEMENT HEART VALVE WITH IMPROVED STITCHING

(71) Applicant: BOSTON SCIENTIFIC SCIMED, INC., Maple Grove, MN (US)

(72) Inventor: Michael Hayes, Salthill (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 15/493,264

(22) Filed: Apr. 21, 2017

(65) Prior Publication Data

US 2017/0304049 A1 Oct. 26, 2017

Related U.S. Application Data

(60) Provisional application No. 62/327,739, filed on Apr. 26, 2016.

(51) Int. Cl.
*A61F 2/24* (2006.01)
*A61B 17/06* (2006.01)
*A61F 2/90* (2013.01)

(52) U.S. Cl.
CPC ...... *A61F 2/2409* (2013.01); *A61B 17/06166* (2013.01); *A61F 2/2403* (2013.01); *A61F 2/2418* (2013.01); *A61F 2/2427* (2013.01); *A61F 2/2445* (2013.01); *A61F 2/2469* (2013.01); *A61B 2017/06171* (2013.01); *A61F 2/90* (2013.01); *A61F 2220/0075* (2013.01); *A61F 2230/0006* (2013.01); *A61F 2250/0069* (2013.01)

(58) Field of Classification Search
CPC .............................................. A61F 2250/0069
See application file for complete search history.

(56) References Cited

U.S. PATENT DOCUMENTS

| 5,411,552 A | 5/1995 | Andersen et al. |
| 2012/0123529 A1* | 5/2012 | Levi ...................... A61F 2/2412 623/2.11 |
| 2013/0090729 A1 | 4/2013 | Gregg et al. |
| 2014/0000112 A1* | 1/2014 | Braido ................. A61F 2/2415 29/890.12 |

(Continued)

FOREIGN PATENT DOCUMENTS

EP 2898858 A1 7/2015

OTHER PUBLICATIONS

International Search Report and Written Opinion dated Jul. 11, 2017 for International Application No. PCT/US207/029552.

*Primary Examiner* — Megan Y Wolf
(74) *Attorney, Agent, or Firm* — Seager, Tufte & Wickhem LLP

(57) ABSTRACT

A replacement heart valve implant may include an expandable anchor member, a plurality of valve leaflets disposed within the anchor member, a seal member disposed about a distal portion of the anchor member, one or more whip sutures attaching a distal end of the seal member to a distal end of the plurality of valve leaflets at a joint, one or more distal lashing sutures attaching a distal portion of the seal member to a distal end of the anchor member, and a plurality of proximal lashing sutures attaching a proximal portion of the seal member to the distal portion of the anchor member, wherein the one or more distal lashing sutures does not extend through the seal member.

7 Claims, 7 Drawing Sheets

(56) References Cited

U.S. PATENT DOCUMENTS

2014/0277417 A1    9/2014   Schraut et al.
2015/0157455 A1    6/2015   Hoang et al.
2015/0320552 A1   11/2015   Letac et al.

* cited by examiner

REPLACEMENT HEART VALVE WITH IMPROVED STITCHING

RELATED APPLICATIONS

This application claims priority to U.S. Provisional Application Ser. No. 62/327,739, filed Apr. 26, 2016.

TECHNICAL FIELD

The present disclosure pertains to medical devices, and methods for manufacturing and/or using medical devices. More particularly, the present disclosure pertains to an improved stitching and/or lashing pattern for a medical device and/or a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a replacement heart valve implant may comprise an expandable anchor member, a plurality of valve leaflets disposed within the anchor member, a seal member disposed about a distal portion of the anchor member, one or more whip sutures attaching a distal end of the seal member to a distal end of the plurality of valve leaflets at a joint, one or more distal lashing sutures attaching a distal portion of the seal member to a distal end of the anchor member, and a plurality of proximal lashing sutures attaching a proximal portion of the seal member to the distal portion of the anchor member, wherein the one or more distal lashing sutures does not extend through the seal member.

In addition, or alternatively, and in a second aspect, the distal end of the seal member includes a reinforcing band coupled to the seal member.

In addition, or alternatively, and in a third aspect, the reinforcing band is at least partially embedded within the seal member.

In addition, or alternatively, and in a fourth aspect, the one or more whip sutures attach the reinforcing band to the distal end of the plurality of valve leaflets.

In addition, or alternatively, and in a fifth aspect, the one or more distal lashing sutures attach the reinforcing band to the distal end of the anchor member.

In addition, or alternatively, and in a sixth aspect, the one or more distal lashing sutures attach the one or more whip sutures to the distal end of the anchor member.

In addition, or alternatively, and in a seventh aspect, the one or more distal lashing sutures directly attach the one or more whip sutures to the distal end of the anchor member.

In addition, or alternatively, and in an eighth aspect, the one or more whip sutures form one or more first helical spirals about the joint.

In addition, or alternatively, and in a ninth aspect, the one or more distal lashing sutures form one or more second helical spirals about the distal end of the anchor member.

In addition, or alternatively, and in a tenth aspect, a suture lattice for a replacement heart valve implant may comprise a whip suture attaching a plurality of valve leaflets to a seal member at a joint, and a distal lashing suture attaching a distal portion of the seal member to a distal end of an expandable anchor member, wherein the distal lashing suture is interwoven with the whip suture.

In addition, or alternatively, and in an eleventh aspect, the plurality of valve leaflets is not directly attached to the anchor member.

In addition, or alternatively, and in a twelfth aspect, the whip suture forms a first spiral oriented in a first direction about the joint.

In addition, or alternatively, and in a thirteenth aspect, the distal lashing suture forms a second spiral oriented in a second direction about the distal end of the anchor member.

In addition, or alternatively, and in a fourteenth aspect, the first direction is the same as the second direction.

In addition, or alternatively, and in a fifteenth aspect, the first direction is opposite the second direction.

In addition, or alternatively, and in a sixteenth aspect, a method of manufacturing a replacement heart valve implant may comprise positioning a tissue subassembly including a plurality of valve leaflets and a seal member relative to an expandable anchor member such that the plurality of valve leaflets is disposed within a lumen of the expandable anchor member and the seal member is disposed at least partially along an outer surface of the anchor member, the expandable anchor member forming a plurality of filament intersections distributed around a circumference of the expandable anchor member, attaching the tissue subassembly to the expandable anchor member, wherein one or more whip sutures attach a distal end of the seal member to a distal end of the plurality of valve leaflets at a joint, and one or more distal lashing sutures attach the seal member to the expandable anchor member distal of a distalmost filament intersection, and attaching a proximal portion of the seal member to a distal portion of the expandable anchor member proximal of the distalmost filament intersection, wherein a plurality of proximal lashing sutures attach the seal member at non-consecutive filament intersections of the expandable anchor member.

In addition, or alternatively, and in a seventeenth aspect, the one or more distal lashing sutures and the one or more whip sutures form a suture lattice.

In addition, or alternatively, and in an eighteenth aspect, the one or more distal lashing sutures attach the one or more whip sutures to a distal end of the expandable anchor member.

In addition, or alternatively, and in a nineteenth aspect, the one or more distal lashing sutures is interwoven with the one or more whip sutures.

In addition, or alternatively, and in a twentieth aspect, the joint is disposed distally of a distal end of the expandable anchor member.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
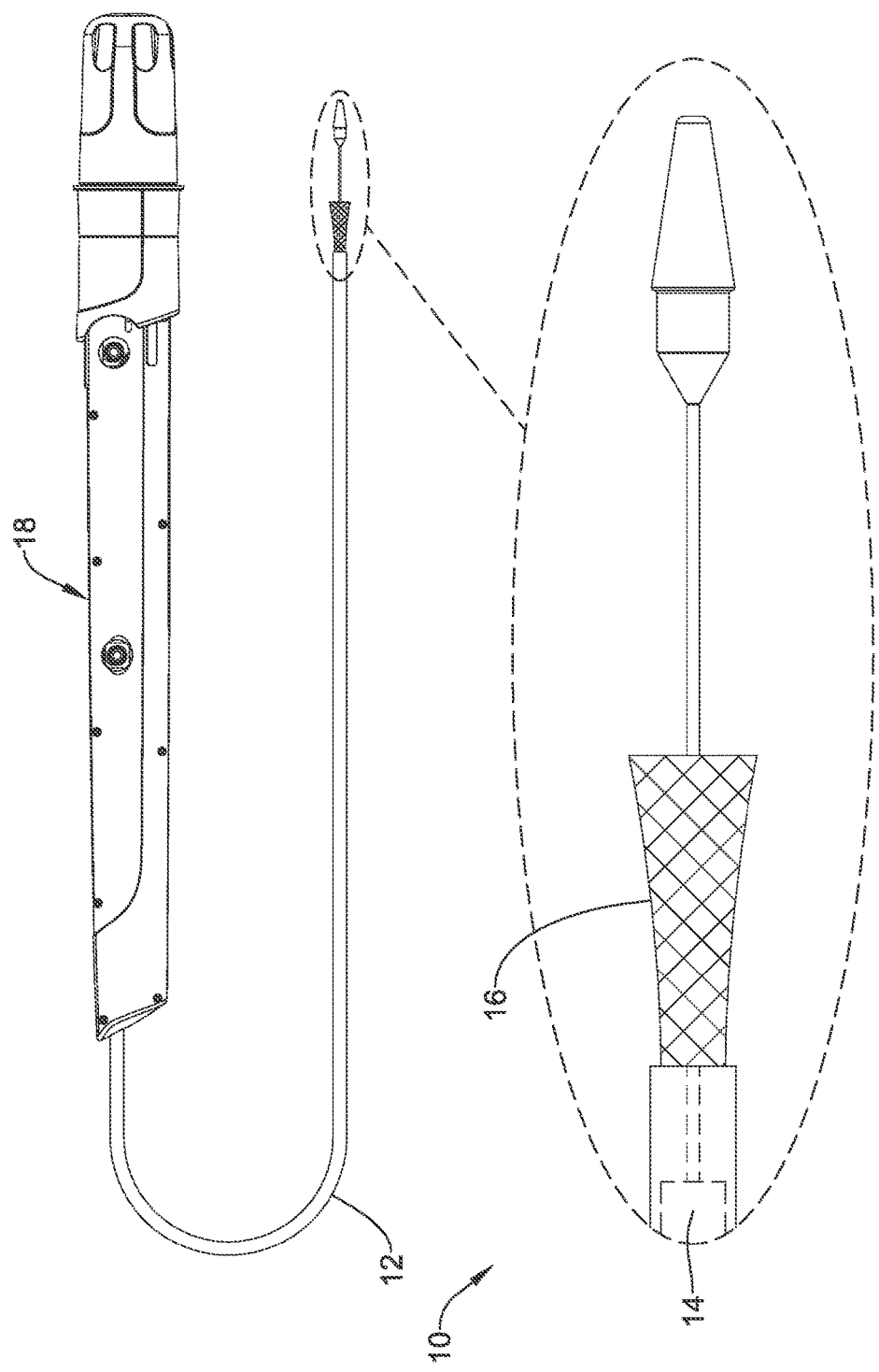
FIG. 1 illustrates an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Generally speaking, in terms of the orientation of the structural elements relative to each other and the operation of the disclosed device(s), a proximal end may be considered closest to the user (or external to a patient) and a distal end farthest from the user (or internal to a patient). However, the skilled artisan will appreciate that the orientations and/or directions may be reversed as necessary or appropriate.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used within a portion of the cardiovascular system in order to diagnose, treat, and/or repair the system. At least some of the medical devices disclosed herein may include a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a replacement heart valve. This, however, is not intended to be limiting as the medical device system 10 may also be used for other interventions including mitral valve replacement, valve repair, valvuloplasty, and the like, or other similar interventions.

The medical device system 10, as seen in FIG. 1 for example, may generally be described as a catheter system that includes a delivery system having an outer sheath 12 for a medical implant 16 (i.e., a replacement heart valve implant, for example, which term may be used interchangeably with the term "medical implant" herein) which may be coupled to the delivery system and disposed within a lumen of the outer sheath 12 during delivery of the medical implant 16. In some embodiments, the delivery system may include an inner catheter 14 extending at least partially through the outer sheath 12 (partially seen in phantom in FIG. 1). In some embodiments, the medical implant 16 may be coupled to the inner catheter 14 and disposed within the lumen of the outer sheath 12 during delivery of the medical implant 16. In some embodiments, a handle 18 may be disposed and/or attached at a proximal end of the delivery system, as seen in FIG. 1, and may include one or more actuation means associated therewith. In some embodiments, the handle 18 may be configured to manipulate the position of the outer sheath 12 relative to the inner catheter 14, and/or aid in the deployment of the medical implant 16. In some embodiments, the medical device system 10 may include a nose cone disposed at a distal end of a guidewire extension tube, wherein the guidewire extension tube may extend distally from the inner catheter 14. In at least some embodiments, the nose cone may be designed to have an atraumatic shape. In some embodiments, the nose cone may include a ridge or ledge that is configured to abut a distal tip of the outer sheath 12 during delivery of the medical implant 16.

Figure 2:
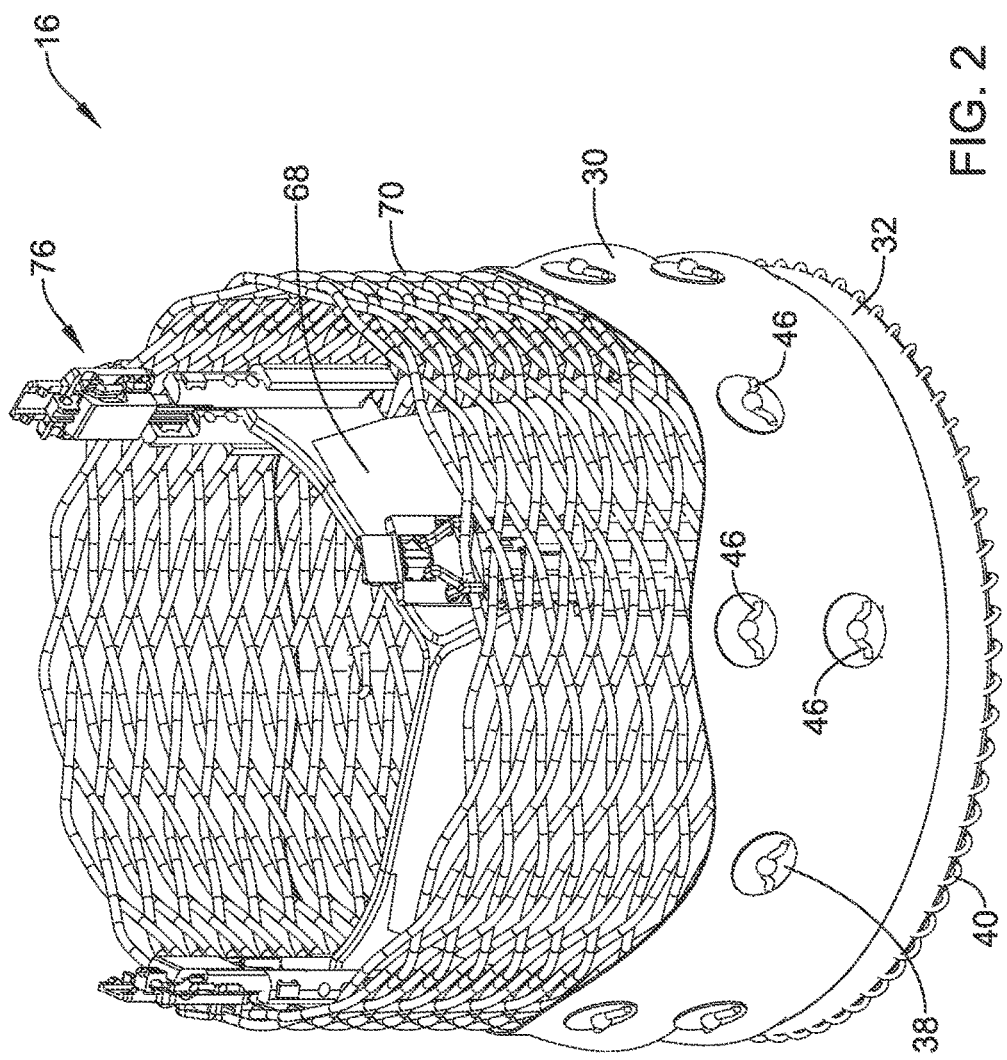
FIG. 2 illustrates an example medical implant associated with an example medical device system.

In use, the medical device system 10 may be advanced percutaneously through the vasculature to a position adjacent to an area of interest or a target location. For example, the medical device system 10 may be advanced through the vasculature and across the aortic arch to a position adjacent to a defective aortic valve. Alternative approaches to treat a defective aortic valve and/or other heart valve(s) are also contemplated with the medical device system 10. During delivery, the medical implant 16 may be generally disposed in an elongated and low profile "delivery" configuration within the delivery system and/or the outer sheath 12 coupled to and/or distal of the inner catheter 14. Once positioned, the outer sheath 12 may be retracted relative to the inner catheter 14, which may be held stationary by the handle 18, and/or the medical implant 16 to expose the medical implant 16. The medical implant 16 may be actuated using the handle 18 in order to translate the medical implant 16 into a generally expanded and larger profile "deployed" configuration suitable for implantation within the anatomy (as seen in FIG. 2, for example). When the medical implant 16 is suitably deployed within the anatomy, the medical implant 16 may be released and/or detached from the medical device system 10, the delivery system can be removed from the vasculature, leaving the medical implant 16 in place in a "released" configuration to function as, for example, a suitable replacement for the native aortic valve. In at least some interventions, the medical implant 16 may be deployed within the native valve (e.g., the native valve is left in place and not excised). Alternatively, the native valve may be removed (such as through valvuloplasty, for example) and the medical implant 16 may be deployed in its place as a replacement.

In some embodiments, the inner catheter 14 may include one or more lumens extending therethrough. For example, in some embodiments, the inner catheter 14 may include a first lumen, a second lumen, a third lumen, and a fourth lumen. Other configurations are also contemplated. In general, the one or more lumens extend along an entire length of the inner catheter 14. Other embodiments are contemplated, however, where one or more of the one or more lumens extend along only a portion of the length of the inner catheter 14. In some embodiments, a distal region of the inner catheter 14 may include a step in outer diameter that defines a decreased diameter section. In some embodiments, the decreased diameter section may define a region where other components of the medical device system 10 may be attached. For example, in some embodiments, a coupler assembly may be attached to the inner catheter 14 at the decreased diameter section and/or at a distal end of the inner catheter 14. In some embodiments, the coupler assembly may releasably couple the medical implant 16 to the inner catheter 14.

In some embodiments, disposed within one of the lumens of the inner catheter 14 may be at least one actuator element, which may be used to actuate (i.e., translate axially or longitudinally, and/or expand) the medical implant 16 between a delivery configuration and a deployed configuration. In some embodiments, the medical device system 10 may include at least one actuator element. In some embodiments, the at least one actuator element may include a plurality of actuator elements, two actuator elements, three actuator elements, four actuator elements, or another suitable or desired number of actuator elements. For the purpose of illustration only, the medical device system 10 and/or the medical implant 16 of FIG. 2 is configured to use three actuator elements (not shown). In use, a proximal end of an actuator element may be connected to the handle 18, and/or manipulated or otherwise actuated by a user using the handle 18, to shift the expandable anchor member 70 and/or the medical implant 16 from a "delivery" configuration to a "deployed" configuration, and later to a "released" configuration. During the release process for the medical implant 16, (e.g., as the medical implant 16 is actuated from the "delivery" configuration to the "deployed" configuration to the "released" configuration), the at least one actuator element may be retracted, withdrawn, and/or translated proximally relative to the inner catheter 14, the medical implant 16, and/or the expandable anchor member 70. Some suitable but non-limiting materials for the actuator element, for example metallic materials or polymeric materials, may be described below.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the actuator element", "the locking element", "the lumen", or other features may be equally referred to all instances and quantities beyond one of said feature. As such, it will be understood that the following discussion may apply equally to any and/or all of the components for which there are more than one within the medical implant 16 (i.e., the at least one actuator element, the plurality of locking elements, etc.) and/or the medical device system 10, unless explicitly stated to the contrary. Additionally, not all instances of some elements or features may be shown in each figure for clarity.

FIG. 2 illustrates some selected components of the medical implant 16. For example, here it can be seen that the medical implant 16 may include a plurality of valve leaflets 68 (e.g., bovine pericardial, polymeric, etc.) which may be secured to an expandable anchor member 70 that is reversibly actuatable between an elongated "delivery" configuration, and an expanded "deployed" configuration. In some embodiments, the expandable anchor member 70 may form a tubular structure defining a central longitudinal axis and a lumen extending through the expandable anchor member 70 along, parallel to, coaxial with, and/or coincident with the central longitudinal axis. In some embodiments, the expandable anchor member 70 may be and/or include a braid formed from one or more filaments or wires (e.g., a single filament or wire, two filaments or wires, etc.). Other configurations are also contemplated. Some suitable but non-limiting materials for the expandable anchor member 70, for example metallic materials or polymeric materials, may be described below. In some embodiments, the expandable anchor member 70 may form a plurality of filament intersections 72 distributed around a circumference of the expandable anchor member 70.

In some embodiments, the medical implant 16 may include a plurality of locking elements 76 attached to the expandable anchor member 70, the plurality of locking elements 76 being configured to lock the expandable anchor member 70 in the "deployed" and/or "released" configuration(s). In some embodiments, at least one actuator element may be configured to actuate the expandable anchor member 70 and/or the medical implant 16 between the "delivery" configuration and the "deployed" configuration and/or the "released" configuration.

In some embodiments, the plurality of locking elements 76 may each comprise an axially movable post member, for example at the commissure portions of the valve leaflets 68 (the post member may sometimes be referred to as a portion of a commissure post, which may serve to secure the valve leaflets 68, or the post member may be connected and/or attached to a commissure post), and a buckle member or other receiving element configured to slidably receive the post member therein to engage with the buckle member and thereafter lock the expandable anchor member 70 and/or the medical implant 16 in the "deployed" and/or the "released" configuration(s). In other words, in at least some embodiments, a medical implant 16 may include a plurality of post members and a corresponding plurality of buckle members. Other configurations and correspondences are also contemplated. Some suitable but non-limiting materials for the buckle member and/or the post member, for example metallic materials or polymeric materials, may be described below.

In some embodiments, the plurality of valve leaflets 68 may be secured to the expandable anchor member 70 at, adjacent to, and/or using (at least in part) individual, corresponding post members. In some embodiments, the plurality of valve leaflets 68 may also be secured to a distal end of the expandable anchor member 70. In at least some embodiments, a distal end of the expandable anchor member 70 may be interchangeably described as an "inflow" end or an "upstream" end of the expandable anchor member 70 and/or the medical implant 16. In some embodiments, the plurality of valve leaflets 68 may be coupled and/or secured (i.e., to the post member, to the expandable anchor member 70, and/or back to themselves) using one or more sutures, threads, wires, filaments, or other suitable elements. In some embodiments, the plurality of valve leaflets 68 may be coupled and/or secured (i.e., to the post member, to the expandable anchor member 70, and/or back to themselves) using an adhesive, a bonding agent, or other suitable securing means. In some embodiments, the plurality of valve leaflets 68 may be coupled and/or secured (i.e., to the post member, to the expandable anchor member 70, and/or back to themselves) using a fabric strip, a textile, or other thin flexible material. In some embodiments, the plurality of valve leaflets 68 may not be directly attached to the expandable anchor member 70.

In some embodiments, the post members and/or the commissure posts may be secured and/or attached to the expandable anchor member 70 (e.g., along the interior of the expandable anchor member) with sutures, tethers, adhesives, or other suitable elements. In some embodiments, the commissure post and/or the post member may include one or more holes or other features provided to aid in securing and/or attaching the commissure post and/or the post member to the expandable anchor member 70.

Positioned adjacent to (e.g., aligned with) the plurality of post members are a corresponding plurality of buckle members, which may be secured and/or fixedly attached to the expandable anchor member 70 (e.g., along the interior of the expandable anchor member 70) with sutures, adhesives, or other suitable mechanisms. In some embodiments, the post member may be axially translatable relative to the buckle member generally parallel to the central longitudinal axis of the expandable anchor member 70 when the post member is at least partially disposed within and/or engaged with the buckle member.

In some embodiments, one buckle member may be fixedly attached to the expandable anchor member 70 adjacent to each of the three post members. Accordingly, in some embodiments, the expandable anchor member 70 may have a total of three buckle members and three post members attached thereto. Similarly, one actuator element may be associated with each post member and buckle member, for a total of three actuator elements in the illustrated example(s). Other embodiments are contemplated where fewer or more buckle members, post members, and/or actuator elements may be utilized.

In some embodiments, a seal member 30 may be circumferentially disposed on and/or about a distal portion of the expandable anchor member 70, as seen in FIG. 2 for example, and as the term suggests, may help to seal an exterior of the medical implant 16 within and/or against a target site or area of interest upon deployment, thereby preventing leakage around the medical implant 16. In some embodiments, the seal member 30 may be disposed about the expandable anchor member 70. In some embodiments, the seal member 30 may be disposed around a perimeter and/or on or against an exterior surface of the expandable anchor member 70. In some embodiments, the seal member 30 may be coupled and/or secured to the expandable anchor member 70.

Figure 3:
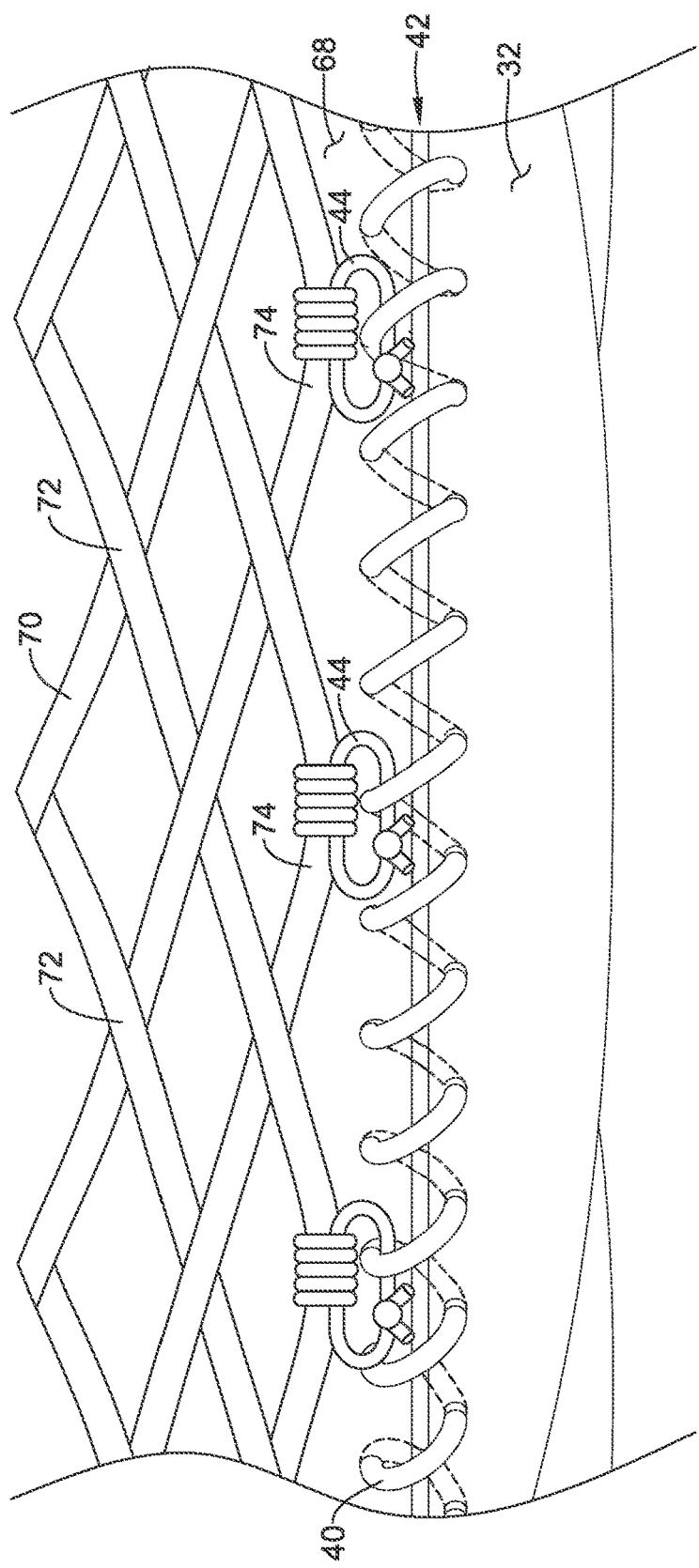
FIG. 3 illustrates a portion of an example medical implant associated with an example medical device system.
Figure 4:
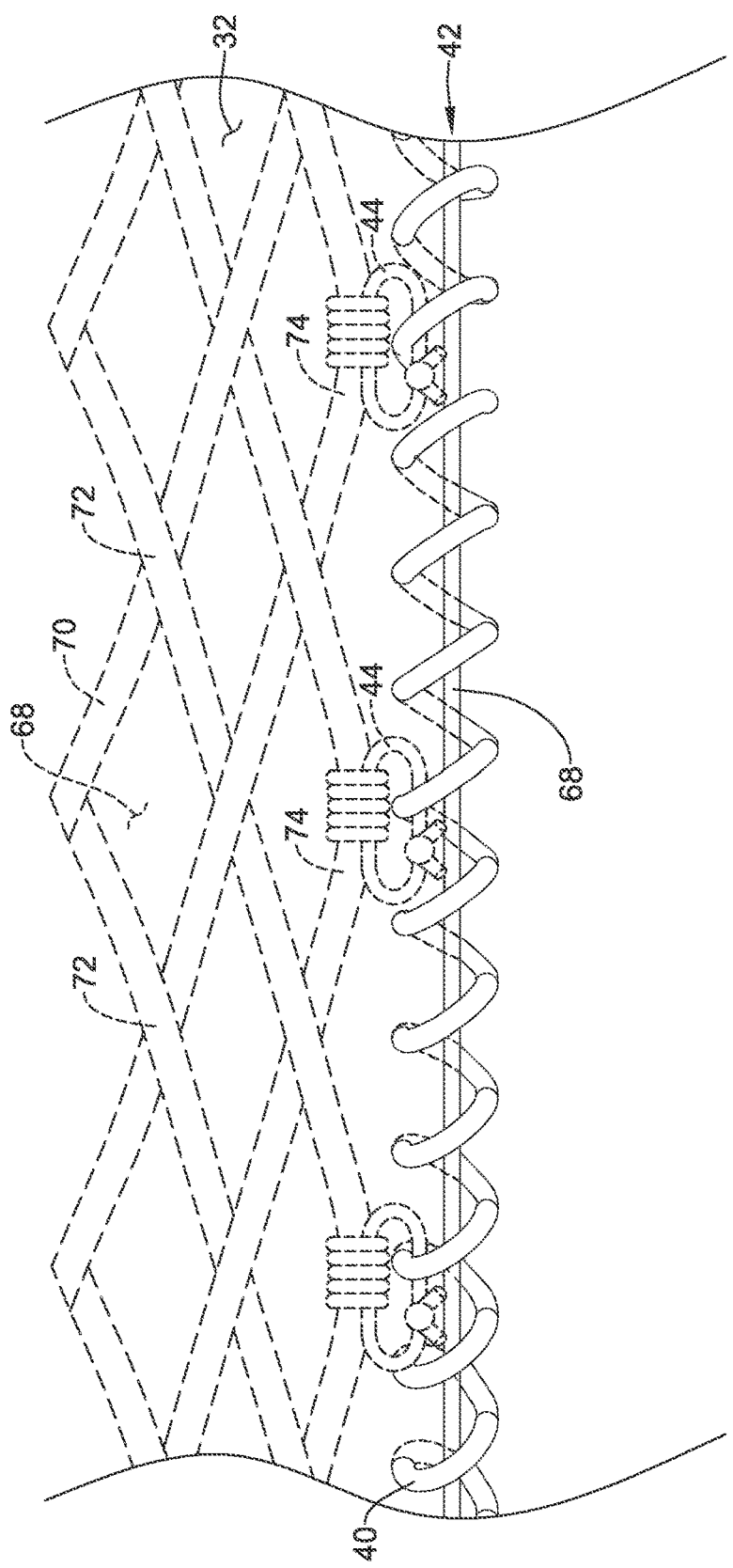
FIG. 4 illustrates a portion of an example medical implant associated with an example medical device system.
Figure 5:
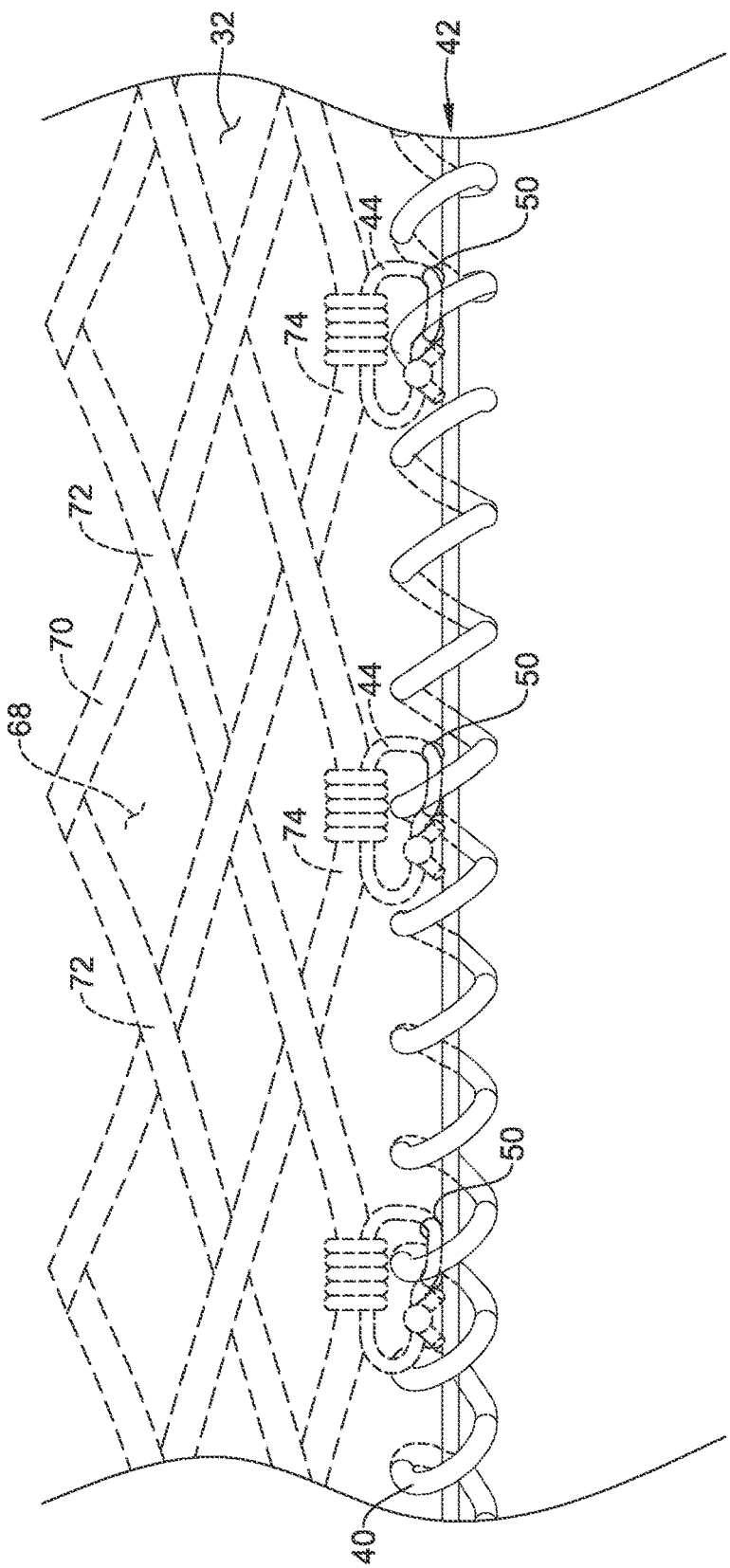
FIG. 5 illustrates a portion of an example medical implant associated with an example medical device system.
Figure 6:
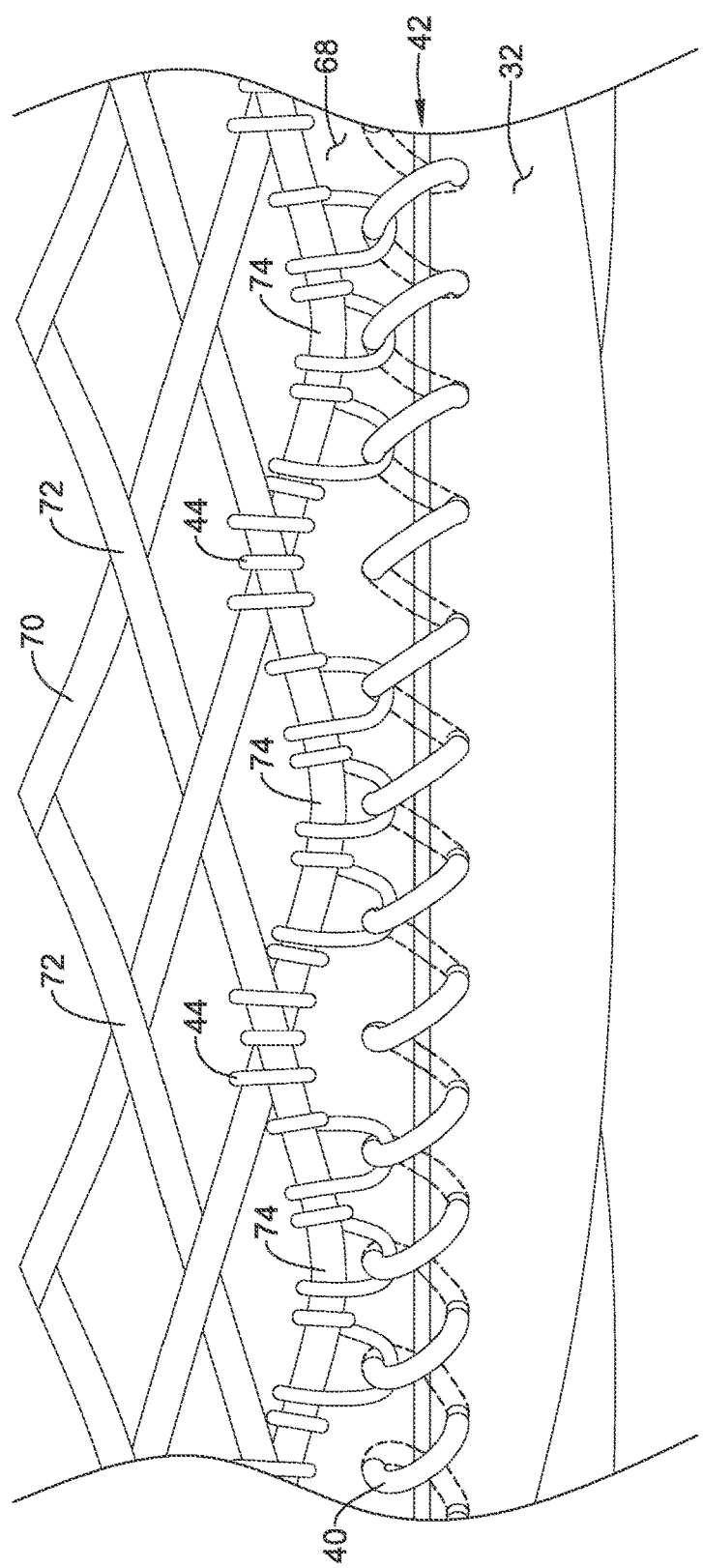
FIG. 6 illustrates a portion of an example medical implant associated with an example medical device system.
Figure 7:
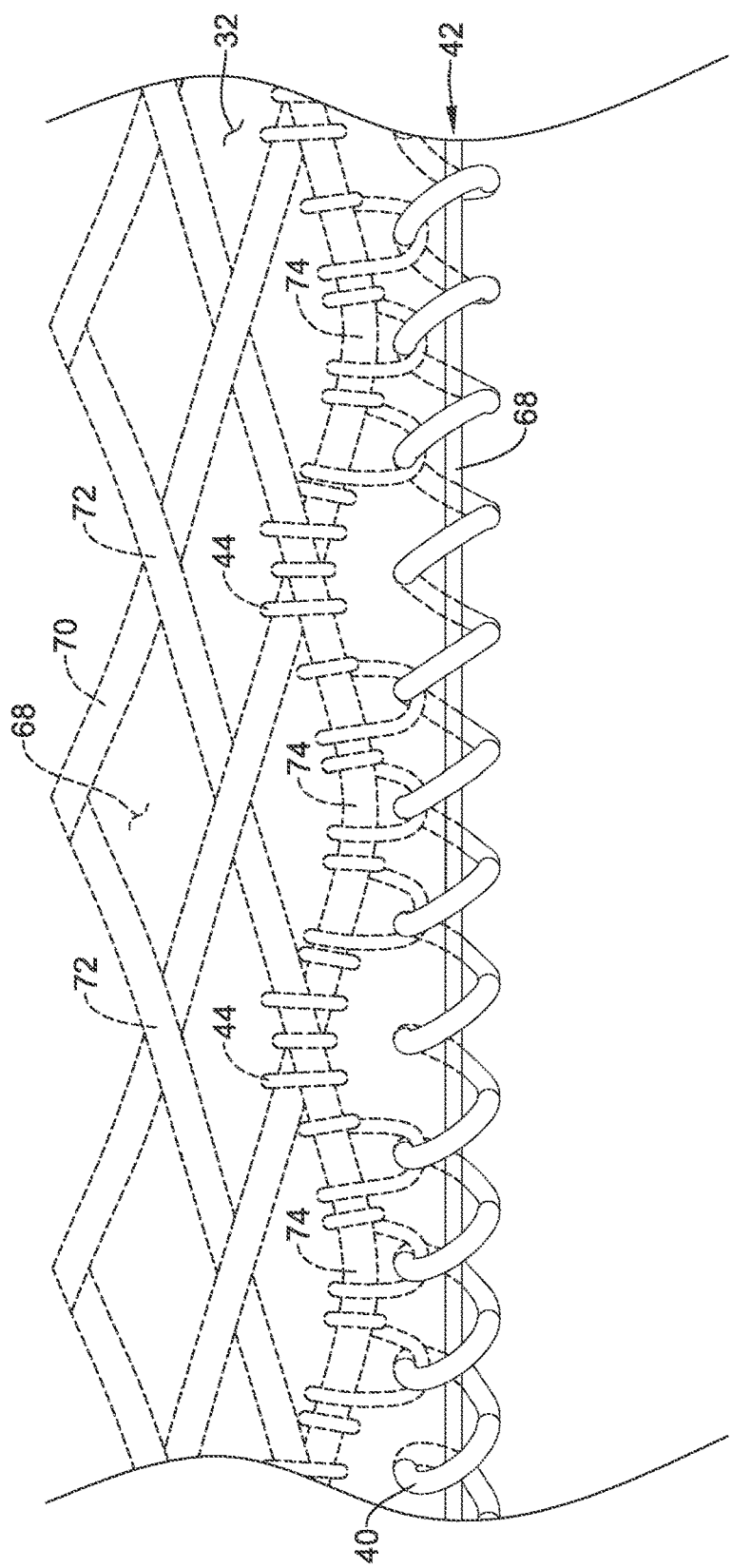
FIG. 7 illustrates a portion of an example medical implant associated with an example medical device system.

For the purpose of illustration and ease of understanding, the seal member 30 shown in FIG. 2 is "pulled down" or "peeled back" approximately 180 degrees about the joint 42 (described further below) in FIGS. 3 and 6. FIGS. 4, 5, and 7 illustrate certain elements in phantom that are "behind" or otherwise "hidden" by the seal member 30 in the view and/or position shown in FIG. 2. FIGS. 3-7 generally illustrate a partial side view looking radially inward toward a central longitudinal axis of the expandable anchor member 70 and/or the medical implant 16.

In some embodiments, the seal member 30 may include a plurality of layers of polymeric material. Some suitable polymeric materials may include, but are not necessarily limited to, polycarbonate, polyurethane, polyamide, polyether block amide, polyethylene, polyethylene terephthalate, polypropylene, polyvinylchloride, polytetrafluoroethylene, polysulfone, and copolymers, blends, mixtures or combinations thereof. Other configurations and/or other suitable materials are also contemplated.

In some embodiments, the modulus of elasticity may vary and/or be different from layer to layer. In other embodiments, the elongation to break may vary and/or be different from layer to layer. In some embodiments, the seal member 30 may also include a reinforcement, a reinforcing layer, and/or one or more reinforcing members added to the polymeric material prior to curing. The reinforcement, the reinforcing layer, and/or the one or more reinforcing members may comprise a woven or nonwoven fabric and may be positioned within or between the various layers. In some embodiments, the reinforcement, the reinforcing layer, and/or the one or more reinforcing members may be positioned on a radially innermost surface or radially outermost surface of the seal member 30. In some embodiments, the reinforcement, the reinforcing layer, and/or the one or more reinforcing members may be generally aligned. In some embodiments, the reinforcement, the reinforcing layer, and/or the one or more reinforcing members may be randomly oriented and/or disposed on the seal member 30.

In some embodiments, a distal end of the seal member 30 may include a reinforcing band 32 coupled to the seal member 30. In some embodiments, the reinforcing band 32 may be integrally formed with, incorporated into, adhered to, and/or at least partially embedded within the seal member 30. In some embodiments, the reinforcing band 32 may be formed from a woven or nonwoven fabric strip, a textile, or other thin flexible material. The reinforcing band 32 may provide tear resistance in the vicinity of sutures, filaments, or other attachment elements associated with components or aspects of the medical implant 16.

In some embodiments, a distal end of each one of the plurality of valve leaflets 68 may be secured directly to the reinforcing band 32 and/or a distal end of the reinforcing band 32. In some embodiments, the plurality of valve leaflets 68 may not be secured directly to the distal end of the expandable anchor member 70. In some embodiments, the reinforcing band 32 may include a plurality of perforations extending through the reinforcing band 32 and/or the seal member 30. In some embodiments, the plurality of perforations may accommodate sutures passing therethrough (e.g., through the reinforcing band 32 and/or the seal member 30) to secure elements or aspects of the medical implant 16, such as (but not limited to) the plurality of valve leaflets 68 and/or the expandable anchor member 70, for example.

In some embodiments, one or more whip sutures 40 may attach a distal end of the seal member 30 to a distal end of the plurality of valve leaflets 68 at a joint 42 adjacent a distal end of the expandable anchor member 70, as seen in FIGS. 2-7 for example. In some embodiments, the one or more whip sutures 40 may attach the reinforcing band 32 and/or a distal end of the reinforcing band 32 to the distal end of the plurality of valve leaflets 68 at a joint 42 adjacent a distal end of the expandable anchor member 70. In some embodiments, the joint 42 may be disposed distally of a distal end of the expandable anchor member 70. In some embodiments, the joint 42 may be disposed distally of a distalmost end of the expandable anchor member 70. In some embodiments, the one or more whip sutures 40 may form one or more first helical spirals oriented in a first direction about the joint 42, as seen in FIGS. 3-7 for example. In some embodiments, the one or more whip sutures 40 may include and/or form a plurality of windings about the joint 42. In some embodiments, the one or more whip sutures 40 may be disposed distally of a distalmost filament, wire, filament intersection, and/or element (e.g., crown) of the expandable anchor member 70. In some embodiments, the one or more whip sutures 40 may be disposed distally of a distal end of the expandable anchor member 70. In some embodiments, the one or more whip sutures 40 may be disposed distally of a distalmost end of the expandable anchor member 70. In some embodiments, a distal end of the expandable anchor member 70 may be disposed and/or positioned at one or more distal crowns 74, for example. In some embodiments, a distalmost end of the expandable anchor member 70 may be disposed and/or positioned at one or more distal crowns 74, for example.

In some embodiments, one or more distal lashing sutures 44 may attach a distal portion of the seal member 30 to a distal end of the expandable anchor member 70. In some embodiments, one or more distal lashing sutures 44 may attach a distal portion of the seal member 30 to a distalmost end of the expandable anchor member 70. In some embodiments, the one or more distal lashing sutures 44 may attach the reinforcing band 32 to the distal end of the expandable anchor member 70. In some embodiments, the one or more distal lashing sutures 44 may attach the reinforcing band 32 to the distalmost end of the expandable anchor member 70. In some embodiments, the one or more distal lashing sutures 44 may attach the one or more whip sutures 40 to the distal end and/or the one or more distal crowns 74 of the expandable anchor member 70, as seen in FIGS. 3-7 for example. In some embodiments, the one or more distal lashing sutures 44 may attach the one or more whip sutures 40 to the distalmost end and/or the one or more distal crowns 74 of the expandable anchor member 70.

In some embodiments, the one or more distal lashing sutures 44 may directly attach the one or more whip sutures 40 to the distal end of the expandable anchor member 70. In some embodiments, the one or more distal lashing sutures 44 may directly attach the one or more whip sutures 40 to the distalmost end of the expandable anchor member 70. In some embodiments, the one or more distal lashing sutures 44 may be interwoven with the one or more whip sutures 40 and/or the plurality of windings of the one or more whip sutures 40 to form a suture lattice. In some embodiments, at least a portion of the one or more distal lashing sutures 44 may be looped through an interior of one or more of the plurality of windings of the one or more whip sutures 40 to form the suture lattice. In some embodiments, the one or more distal lashing sutures 44 may form one or more second helical spirals oriented in a second direction about the distal end of the expandable anchor member 70. In some embodiments, the one or more distal lashing sutures 44 may form one or more second helical spirals oriented in a second direction about the distalmost end of the expandable anchor member 70. In some embodiments, the first direction may be the same as the second direction. In some embodiments, the first direction may be opposite the second direction.

In some embodiments, the one or more distal lashing sutures 44 do not extend through the seal member 30 and/or the reinforcing band 32, as seen in FIGS. 3 and 4 for example. In other words, in some embodiments, the one or more distal lashing sutures 44 may not pass through the plurality of perforations and/or through a thickness or a wall of the seal member 30 and/or the reinforcing band 32. In some embodiments, the one or more distal lashing sutures 44 may attach a distal end of the seal member 30 to the expandable anchor member 70 distal of a distalmost filament intersection 72 and/or at the one or more distal crowns 74. In some embodiments, the one or more distal lashing sutures 44 may attach a distal end of the seal member 30 to the expandable anchor member 70 at the distalmost filament intersection(s) 72 and distally of the distalmost filament intersection(s) 72. In some embodiments, the one or more distal lashing sutures 44 may be disposed between the seal member 30 and/or the reinforcing band 32 and the plurality of valve leaflets 68.

In some embodiments, at least a portion of each of the one or more distal lashing sutures 44 may extend radially outward through the plurality of perforations and/or through a thickness or a wall of the seal member 30 and/or the reinforcing band 32, for example at a first hole or aperture 50, under one or more of the plurality of windings of the one or more whip sutures 40, and radially back inward through a second hole or aperture 50, thereby forming an interlocking and/or interwoven arrangement between the one or more distal lashing sutures 44 and the one or more whip sutures 40, as seen in FIG. 5 for example. In some embodiments, the one or more distal lashing sutures 44 may be secured in place and/or back to itself with a knot or other fastening element. In some embodiments, ends of the one or more distal lashing sutures 44 forming the knot or other fastening element may be melted, adhesively bonded, or otherwise fused to each other to form a permanent attachment therebetween. In some embodiments, the knot or other fastening element may be disposed radially outward of the seal member 30 and/or the reinforcing band 32, as seen in FIG. 5 for example. In some embodiments, the knot or other fastening element may be disposed between the plurality of valve leaflets 68 and the seal member 30 and/or the reinforcing band 32, and/or may be disposed radially inward of the seal member and/or the reinforcing band 32, as seen in FIGS. 4 and 7 for example.

As noted above, in some embodiments, the one or more distal lashing sutures 44 may be interwoven with the one or more whip sutures 40 to form a suture lattice, as seen in FIGS. 6-7 for example. In some embodiments, the one or more distal lashing sutures 44 may include and/or form a plurality of windings about the expandable anchor member 70 and/or individual elements thereof—a distal end, a distalmost filament, and/or a distal crown 74, for example. In some embodiments, the one or more distal lashing sutures 44 may include and/or form a plurality of windings about the distalmost filament intersection(s) 72. In some embodiments, the plurality of windings of the one or more distal lashing sutures 44 may be interwoven with the one or more whip sutures 40 at every other winding of the one or more distal lashing sutures 44 along at least a portion of the one or more distal lashing sutures 44 and/or the one or more whip sutures 40. In some embodiments, the plurality of windings of the one or more whip sutures 40 may be interwoven with the one or more distal lashing sutures 44 at adjacent and/or every winding of the one or more whip sutures 40 along at least a portion of the one or more distal lashing sutures 44 and/or the one or more whip sutures 40. In some embodiments, some of the plurality of windings of the one or more distal lashing sutures 44 may be interwoven with several adjacent windings of the one or more whip sutures 40. In some embodiments, groups of adjacent interwoven windings may be spaced apart by one or more of the plurality of windings of the one or more whip sutures 40 and/or one or more of the plurality of windings of the one or more distal lashing sutures 44.

In some embodiments, a plurality of proximal lashing sutures 46 may attach a proximal portion of the seal member 30 to the distal portion of the expandable anchor member 70, as seen in FIG. 2 for example. In some embodiments, a grommet 38 may be disposed along an outer surface of the seal member 30 and/or at least partially embedded within the seal member 30 at each of the plurality of proximal lashing sutures 46 to aid in attaching the seal member 30 to the expandable anchor member 70. In some embodiments, the plurality of proximal lashing sutures 46 may extend through the grommet(s) 38. In some embodiments, the plurality of proximal lashing sutures 46 may attach the proximal portion of the seal member 30 to the distal portion of the expandable anchor member 70 proximal of the distalmost filament intersection 72 and/or the one or more distal crowns 74. In some embodiments, the plurality of proximal lashing sutures 46 may attach the proximal portion of the seal member 30 to the expandable anchor member 70 at non-consecutive filament intersections 72, as may be seen in FIG. 2 for example. In some embodiments, the plurality of proximal lashing sutures 46 may attach the proximal portion of the seal member 30 to the expandable anchor member 70 only at non-consecutive filament intersections 72 of the expandable anchor member 70.

In some embodiments, a method of manufacturing a medical implant 16 and/or a replacement heart valve implant may include positioning a tissue subassembly including a plurality of valve leaflets 68 and a seal member 30 relative to an expandable anchor member 70 such that the plurality of valve leaflets 68 is disposed within a lumen of the expandable anchor member 70 and the seal member 30 is disposed at least partially along an outer surface of the expandable anchor member 70, the expandable anchor member 70 forming a plurality of filament intersections 72 distributed around a circumference of the expandable anchor member 70. In some embodiments, one or more whip sutures 40 may attach a distal end of the seal member 30 to a distal end of the plurality of valve leaflets 68 at a joint 42. In some embodiments, the tissue subassembly may be assembled and/or formed prior to positioning the tissue subassembly relative to the expandable anchor member 70.

In some embodiments, a method of manufacturing a medical implant 16 and/or a replacement heart valve implant may include attaching the tissue subassembly to the expandable anchor member 70 after positioning the tissue subassembly relative to the expandable anchor member 70. In some embodiments, one or more distal lashing sutures 44 may attach the seal member 30 to the expandable anchor member 70 distal of a distalmost filament intersection 72. In some embodiments, the one or more distal lashing sutures 44 may attach the one or more whip sutures 40 to a distal end (e.g., to a distal crown 74) of the expandable anchor member 70. In some embodiments, the one or more distal lashing sutures 44 may directly attach the one or more whip sutures 40 to a distal end (e.g., to a distal crown 74, to each distal crown 74, etc.) of the expandable anchor member 70. In some embodiments, the one or more whip sutures 40 may be interwoven with the one or more distal lashing sutures 44 to form a suture lattice.

In some embodiments, a method of manufacturing a medical implant 16 and/or a replacement heart valve implant may include forming a first helical spiral in a first direction about the joint 42 with the one or more whip sutures 40. In some embodiments, a method of manufacturing a medical implant 16 and/or a replacement heart valve implant may include forming a second helical spiral in a second direction about the joint 42 with the one or more distal lashing sutures 44. In some embodiments, the first direction may be the same as the second direction. In some embodiments, the first direction may be opposite the second direction.

In some embodiments, a method of manufacturing a medical implant 16 and/or a replacement heart valve implant may include attaching a proximal portion of the seal member 30 to a distal portion of the expandable anchor member 70 proximal of the distalmost filament intersection 72. In some embodiments, a plurality of proximal lashing sutures 46 may attach the proximal portion of the seal member 30 to the distal portion of the expandable anchor member 70 at non-consecutive filament intersections 72 of the expandable anchor member 70. In some embodiments, the plurality of proximal lashing sutures 46 may attach the proximal portion of the seal member 30 to the distal portion of the expandable anchor member 70 only at non-consecutive filament intersections 72 of the expandable anchor member 70.

The materials that can be used for the various components of the medical device system 10 (and/or other systems disclosed herein) and the various elements thereof disclosed herein may include those commonly associated with medical devices. For simplicity purposes, the following discussion makes reference to the delivery system and/or the medical implant 16. However, this is not intended to limit the devices and methods described herein, as the discussion may be applied to other elements, members, components, or devices disclosed herein, such as, but not limited to, the expandable anchor member 70 and/or elements or components thereof.

In some embodiments, the medical device system 10, the delivery system, and/or the medical implant 16, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery system and/or the medical implant 16, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MM) compatibility is imparted into the medical device system 10. For example, the delivery system and/or the medical implant 16, and/or components or portions thereof, may be made of a material that does not substantially distort the image and create substantial artifacts (i.e., gaps in the image). Certain ferromagnetic materials, for example, may not be suitable because they may create artifacts in an MRI image. The delivery system and/or the medical implant 16, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, an exterior surface of the medical device system 10 (including, for example, an exterior surface of the delivery system) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the outer sheath, or in embodiments without an outer sheath over portions of the delivery system, or other portions of the medical device system 10. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A replacement heart valve implant, comprising:
   an expandable anchor member;
   a plurality of valve leaflets disposed within the anchor member;
   a seal member disposed about a distal portion of the anchor member;
   one or more whip sutures attaching a distal end of the seal member to a distal end of the plurality of valve leaflets at a joint;
   one or more distal lashing sutures attaching a distal portion of the seal member to a distal end of the anchor member,
wherein the one or more distal lashing sutures directly attach the one or more whip sutures to the distal end of the anchor member; and
a plurality of proximal lashing sutures attaching a proximal portion of the seal member to the distal portion of the anchor member;
wherein the one or more distal lashing sutures does not extend through the seal member.

2. The replacement heart valve implant of claim 1, wherein the distal end of the seal member includes a reinforcing band coupled to the seal member.

3. The replacement heart valve implant of claim 2, wherein the reinforcing band is at least partially embedded within the seal member.

4. The replacement heart valve implant of claim 2, wherein the one or more whip sutures attach the reinforcing band to the distal end of the plurality of valve leaflets.

5. The replacement heart valve implant of claim 2, wherein the one or more distal lashing sutures attach the reinforcing band to the distal end of the anchor member.

6. The replacement heart valve implant of claim 1, wherein the one or more whip sutures form one or more first helical spirals about the joint.

7. The replacement heart valve implant of claim 6, wherein the one or more distal lashing sutures form one or more second helical spirals about the distal end of the anchor member.

* * * * *